United States Patent
Li et al.

(10) Patent No.: US 11,378,636 B2
(45) Date of Patent: Jul. 5, 2022

(54) LOCAL SHIMMING SYSTEM FOR MAGNETIC RESONANCE IMAGING

(71) Applicant: SHENZHEN INSTITUTES OF ADVANCED TECHNOLOGY, Nanshan Shenzhen (CN)

(72) Inventors: Ye Li, Nanshan Shenzhen (CN); Qiaoyan Chen, Nanshan Shenzhen (CN); Jo Lee, Nanshan Shenzhen (CN); Chao Luo, Nanshan Shenzhen (CN); Jianhong Wen, Nanshan Shenzhen (CN); Chao Zou, Nanshan Shenzhen (CN); Xin Liu, Nanshan Shenzhen (CN)

(73) Assignee: SHENZHEN INSTITUTES OF ADVANCED TECHNOLOGY, Nanshan Shenzhen (CN)

( * ) Notice: Subject to any disclaimer, the term of this patent is extended or adjusted under 35 U.S.C. 154(b) by 0 days.

(21) Appl. No.: 17/032,588

(22) Filed: Sep. 25, 2020

(65) Prior Publication Data
US 2021/0088611 A1    Mar. 25, 2021

Related U.S. Application Data

(60) Division of application No. 16/261,610, filed on Jan. 30, 2019, now Pat. No. 10,969,449, which is a
(Continued)

(51) Int. Cl.
*G01R 33/3875* (2006.01)
*G01R 33/44* (2006.01)
(Continued)

(52) U.S. Cl.
CPC .......... *G01R 33/3875* (2013.01); *A61B 5/055* (2013.01); *G01R 33/443* (2013.01);
(Continued)

(58) Field of Classification Search
CPC ........................ G01R 33/3875; G01R 33/443; G01R 33/543; G01R 33/4814; G01R 33/243;
(Continued)

(56) References Cited

U.S. PATENT DOCUMENTS

| 9,360,541 B2 | 6/2016 | Bieber |
| 9,817,097 B2 | 11/2017 | van Beek et al. |

(Continued)

FOREIGN PATENT DOCUMENTS

| CN | 1934458 A | 3/2007 |
| CN | 101604008 A | 12/2009 |

(Continued)

OTHER PUBLICATIONS

Wharton, Iain P., et al. "Design and development of a prototype endocavitary probe for high-intensity focused ultrasound delivery with integrated magnetic resonance imaging." Journal of Magnetic Resonance Imaging. pp. 548-556 (Year: 2007).*

(Continued)

*Primary Examiner* — Rishi R Patel
(74) *Attorney, Agent, or Firm* — Cantor Colburn LLP

(57) ABSTRACT

A shimming system for magnetic resonance imaging is provided, which includes: a multi-channel local shim coil unit configured to be installed on an inspection table of a magnetic resonance imaging system, where the multi-channel local shim coil unit includes a local multi-channel shim coil and a radio frequency receiving coil for receiving magnetic resonance signals, and the radio frequency receiving coil is placed inside the local multi-channel shim coil and separated by a distance from the local multi-channel shim coil; a computer control system configured to install and set software controlled by a DC power and calculate field maps and calculate optimization processes; a DC power system communicatively connected to the computer control (Continued)

system to control a value of current of each channel; and a housing having a semi-cylindrical configuration, where the local multi-channel shim coil is only distributed on a semi-cylindrical surface of the semi-cylindrical configuration of the housing.

5 Claims, 5 Drawing Sheets

Related U.S. Application Data continuation of application No. PCT/CN2017/118275, filed on Dec. 25, 2017.

(51) Int. Cl.
  *G01R 33/54* (2006.01)
  *A61B 5/055* (2006.01)
  *G01R 33/48* (2006.01)
  *A61B 17/32* (2006.01)
  *G01R 33/24* (2006.01)

(52) U.S. Cl.
  CPC ....... *G01R 33/4814* (2013.01); *G01R 33/543* (2013.01); *A61B 17/320068* (2013.01); *A61B 2017/320069* (2017.08); *G01R 33/243* (2013.01); *G01R 33/4804* (2013.01)

(58) Field of Classification Search
  CPC .................. G01R 33/4804; G01R 33/4808; A61B 5/055; A61B 2017/320069; A61B 17/320068
  See application file for complete search history.

(56) References Cited

U.S. PATENT DOCUMENTS

| | | | |
|---|---|---|---|
| 9,851,423 | B2 | 12/2017 | Biber et al. |
| 10,335,035 | B2 | 7/2019 | Biber et al. |
| 2007/0279060 | A1 | 12/2007 | Dannels et al. |
| 2012/0249137 | A1 | 10/2012 | Witschey |
| 2013/0190608 | A1* | 7/2013 | Schmidt ............... G01R 33/341 600/422 |
| 2015/0301135 | A1 | 10/2015 | Bieber et al. |
| 2015/0355306 | A1 | 12/2015 | Stemmer |
| 2019/0195972 | A1 | 6/2019 | Li et al. |
| 2020/0271736 | A1* | 8/2020 | Han ................... G01R 33/3635 |

FOREIGN PATENT DOCUMENTS

| | | | |
|---|---|---|---|
| CN | 102508182 | A | 6/2012 |
| CN | 102830377 | A | 12/2012 |
| CN | 103529411 | A | 1/2014 |
| CN | 104422915 | A | 3/2015 |
| CN | 104502873 | A | 4/2015 |
| CN | 104573308 | A | 4/2015 |
| CN | 105044636 | A | 11/2015 |
| CN | 105467337 | A | 4/2016 |
| JP | 10127599 | A | 5/1998 |
| JP | 11318517 | | 11/1999 |
| WO | 2004036229 | A3 | 9/2004 |

OTHER PUBLICATIONS

International Search Report for Application No. PCT/CN2017/118275.

"Magnetic field modeling with a set of individual localized coils", Journal of Magnetic Resonance, 2010, 204(2): 281-289 by Juchem C et al.

Multicoil shimming of the mouse brain[J]. Magnetic resonance in medicine, 2011, 66(3): 893-900 by Juchem C et al.

* cited by examiner

LOCAL SHIMMING SYSTEM FOR MAGNETIC RESONANCE IMAGING

CROSS-REFERENCE TO RELATED APPLICATION

This application is a divisional application of U.S. patent application Ser. No. 16/261,610 filed on Jan. 30, 2019, which is a continuation of PCT Application No. PCT/CN2017/118275 filed on Dec. 25, 2017, the contents each of which are incorporated herein by reference thereto.

TECHNICAL FIELD

The present application relates to the field of magnetic resonance imaging technology, and more particularly to a local shimming system for magnetic resonance imaging and the shimming method thereof.

BACKGROUND

In a magnetic resonance imaging system, the magnet itself is generally capable of providing a relatively homogeneous static magnetic field B0 in a certain space. However, due to the difference in magnetic susceptibility of the tissue, local magnetic field changes are generated at the interface, causing image artifacts. Especially in single-shot spin Echo-planar imaging (EPI), geometric distortion, signal loss and image blur will occur. In general, increasing the number of shim coils can reduce the non-homogeneity of the magnetic field, thereby improving the quality of the image.

In general, shim coils mainly include two types: spherical harmonic function (SH) shim coils and multi-coil (MC) shim coils. The SH shim coil is generally used for the magnetic field non-homogeneity correction of the main magnet, while the SH shim coil of the commercial MRI system has the second order at most. In animal and human brain experiments, the magnetic field non-homogeneity at the junction of tissue and air is often as high as 5 orders, so the order of the SH shim coil needs to be increased to 5 orders to achieve a better shimming effect. However, increasing the order of the SH shim coils brings about practical problems, such as reduction of efficient space, poor efficiency of the coil. Moreover, an additional cooling system for shim coils and the need to increase the number of power amplifiers should be considered. Compared with the SH shim coil, the MC shim coil generates a relatively complex high-order magnetic field with a plurality of simple coil loops, obtaining a better shimming capability. Moreover, the inductance of the MC shim coil is relatively small, and is far away from the main magnet, without causing a large eddy current.

At present, in magnetic resonance imaging, the more is the number of the shimming multi-coil units, the higher is the order of the non-uniform magnetic field that can be compensated. However, the problem is that more power amplifiers are needed; moreover, in the shimming process, it is necessary to perform sensitivity field map collection for each channel coil unit, which takes long time.

For example, CN 201510629760 discloses a shim coil device that compensates for non-homogeneity of a main magnetic field in the process of performing medical magnetic resonance imaging of human chest. CN201210202891, CN201410414924 and CN201510173911 have also developed shimming systems for magnetic resonance imaging of human head and abdomen. The papers "*Magnetic field modeling with a set of individual localized coils*", Journal of Magnetic Resonance, 2010, 204(2): 281-289 by Juchem C et al., and "*Multicoil shimming of the mouse brain[J]*. Magnetic resonance in medicine", 2011, 66(3): 893-900 by Juchem C et al., describe a shim coil applied to magnetic resonance imaging in mouse brains, in which the number of channels is from 24 to 48, and the number of power amplifiers is also from 24 to 48, the cost is much higher and the system is more complicated.

In view of this, a local shimming system and a process capable of achieving a better shimming effect using a shim coil with a small number of channels should be developed.

SUMMARY

In view of the deficiencies of the above techniques, it is an object of the present application to provide a magnetic resonance imaging system applicable to animals and the method thereof, meanwhile the system and method are applicable for magnetic resonance temperature imaging. The present application specifically provides a local shimming system that can be used for magnetic resonance imaging and a shimming method to reduce high-order non-uniform magnetic field shift and improve the homogeneity of the B0 magnetic field. The local shim coils are asymmetrically distributed with a smaller number of channels to solve the problem of non-homogeneity of the B0 magnetic field during the process of magnetic resonance imaging. The local shimming method of the present application uses a fast two-dimensional gradient echo sequence to collect the field mapping B0, which is relatively short in time and relatively simple.

In order to achieve the above object, in view of the deficiencies in the prior art, the present application provides a shimming method for magnetic resonance imaging, wherein the method comprises the steps of: collecting B0 field map information using a two-dimensional gradient echo; calculating and evaluating the homogeneity of B0; optimizing the current of each channel of the shim coil; determining whether the minimum standard deviation value of Δf is obtained; outputting an optimal current combination value and setting optimum current values corresponding to each channel shimming coil on the current control software; and testing and evaluating the homogeneity of B0 to achieve the shimming goal.

In some embodiments, the collecting comprises collecting the field map information with the pulse sequence echo number of 5, the pulse sequence repetition time of 25 ms, and the flip angle of 10°. The calculating comprises unwrapping five echo phase maps, and performing straight-line fitting of the pixel points at the same position of the five phase maps on the five corresponding echo times TE by using the least square method, wherein the slope value is the main magnetic field offset value, and the calculation formula is:

$$\Delta f = \frac{\Delta \phi}{2\pi \cdot \Delta TE}$$

wherein Δφ is the phase difference between the two echoes, γ is the gyromagnetic ratio of the imaging nucleus, and ΔTE is the time difference between the two echoes.

In some embodiments, the step of optimizing the current values of the shim coil comprises linearly combining the main magnetic field offset value $\Delta f_0$ and the sensitivity field map $\Delta f_{0i}$ of each channel shim coil to achieve the minimum standard deviation value of Δf, and the main magnetic field offset value Δf after the shimming current is applied is expressed as:

$$\Delta f = \Delta f_0 + \sum_{i=1}^{n} a_i \cdot \Delta f_{0i}$$

wherein I=1, 2, . . . , n, and n is the number of channels of the shim coil, $\Delta f_0$ is the main magnetic field offset value without applying the shimming current, $\Delta f_{0i}$ is the sensitivity field map of the shim coil, and $a_i$ is the linear superposition factor of the shim coil sensitivity field map.

The present application further provides a local shimming system for magnetic resonance imaging, which comprises a multi-channel local shim coil unit, which is configured to be installed on an inspection table of the magnetic resonance imaging system, wherein the local shimming coil unit comprises a local multi-channel shimming coil and a radio frequency receiving coil for receiving magnetic resonance signals, and the radio frequency receiving coils are placed inside the local multi-channel shim coil with a separated distance; a computer control system, which is configured to install and set the software controlled by the DC power and calculate field maps in the calculation and optimization processes; and a DC power system, which is communicatively connected to the computer control system to control the amount of current of each channel.

In some embodiments, the multi-channel local shim coil unit further comprises a housing, and the housing is provided with a plurality of holes for the tuning and matching of the radio frequency receiving coil. In some embodiments, the multi-channel local shim coil unit comprises 5 channels of local shim coils, and the local shim coils are asymmetrically distributed.

In some embodiments, the local shim coil is a circular loop with a diameter of 4 cm. In some embodiments, the bottom of the housing is further provided with a hole as a reserved channel for the ultrasound ablation treatment. In some embodiments, the hole has a diameter of 6 cm.

The local shimming system and the shimming method of the present application provide at least the following advantages:

a better shimming effect is achieved using a shim coil with a smaller number of channels, the system is simpler and the cost is relatively low;

the proposed shimming method is relatively simple and is relatively short in time; and the system is applicable to magnetic resonance temperature imaging, improving the accuracy of temperature measurement.

These and other advantages of the present application will be understood by those skilled in the art upon reading the entire specification and claims.

BRIEF DESCRIPTION OF THE DRAWINGS

The drawings described in the present application are intended to provide a further understanding of the present application and are not intended to limit the present application. In the drawing.

In the figures: 10 represents a multi-channel local shim coil unit, 11 represents a magnetic resonance imaging system, 101 represents an operation room, 102 represents an equipment room, 103 represents a magnetic resonance laboratory, 104 represents a computer control system, 105 represents a network cable, 106 represents a DC power system, 107 represents a waveguide plate and a waveguide tube, 108 represents a DC power cord, 109 represents a local multi-channel shim coil, 110 represents an RF receiving coil.

DESCRIPTION OF THE EMBODIMENTS

Specific embodiments of the present application will be described below with reference to the accompanying drawings. In the specific embodiments of the present application described hereinafter, some very specific technical features are described for a better understanding of the present application, but it will be apparent to those skilled in the art that not all of the technical features are essential technical features for implementing the present application. Some specific embodiments of the present application described below are merely some exemplary embodiments of the present application and are not to be construed as limiting the present application.

Figure 1:
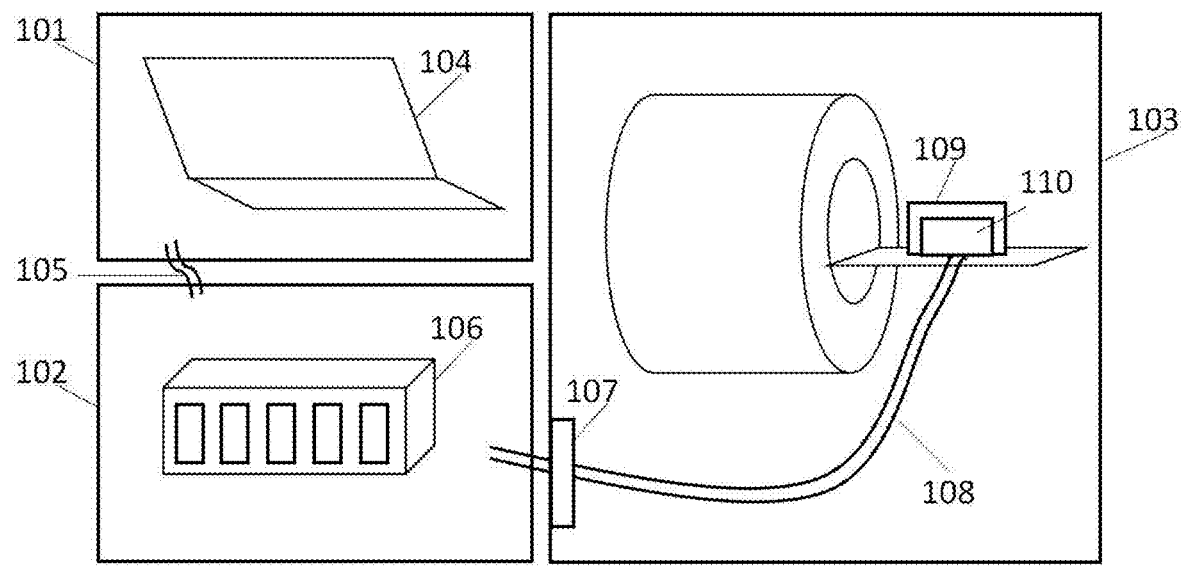
FIG. 1 is a schematic structural diagram of the local shimming system for magnetic resonance imaging according to an embodiment of the present application.

FIG. 1 schematically illustrates a local shimming system for magnetic resonance imaging according to an embodiment of the present application. In the present embodiment, the local shimming system includes a multi-channel local shim coil unit 10, a DC power system 106, and a computer control system 104. The multi-channel local shim coil unit 10 can be installed on an inspection table of the magnetic resonance imaging system 11 and connected to the DC power system 106 via a DC power line 108 through a waveguide plate and a waveguide tube 107. The role of the waveguide plate and the waveguide tube is to reduce noise. The multi-channel local shim coil unit 10 includes a local multi-channel shim coil 109 and a radio frequency receiving coil 110 for receiving magnetic resonance signals. The RF receiving coil 110 can be placed inside the local multi-channel shim coil 109 with a distance ranging from 1 cm to 2 cm. The DC power system 106 is communicably connected to the computer control system 104. In some embodiments, computer control system 104 may be configured to install and set the software system controlled by the DC power and calculate the field maps and calculate optimization processes. The network cable 105 is configured to connect the computer to the DC power system 106.

Figure 2:
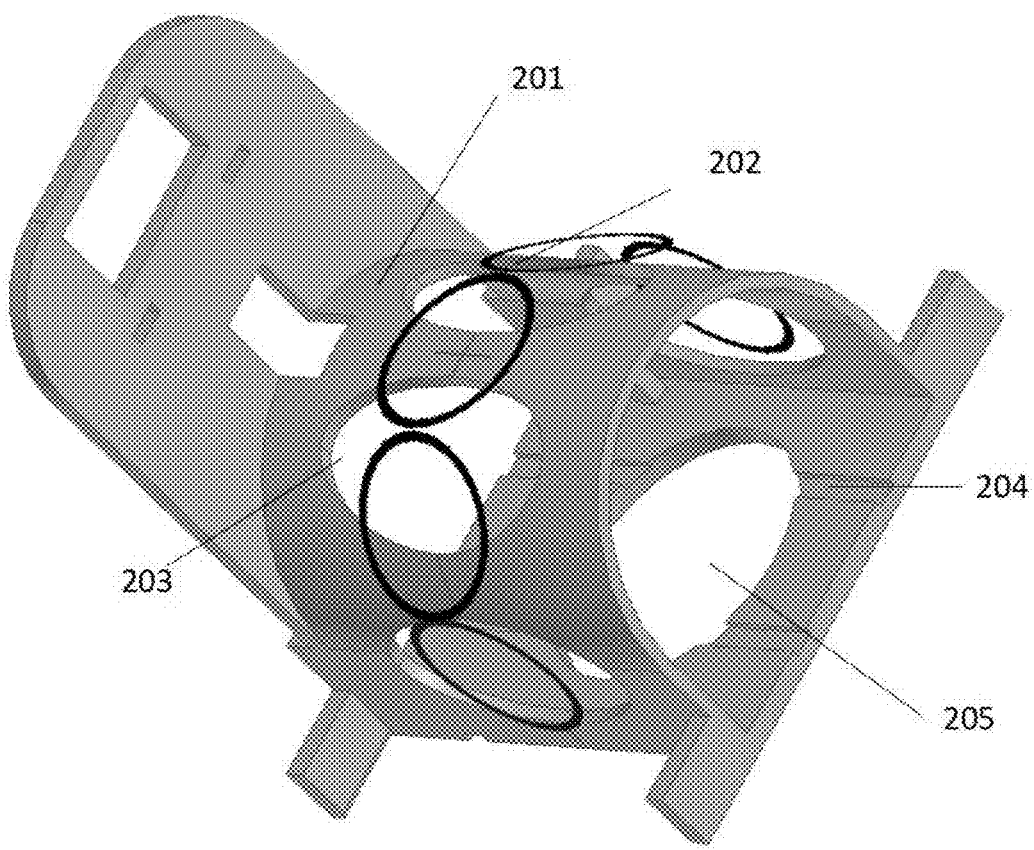
FIG. 2 is a schematic perspective structural diagram of the multi-channel local shim coil unit according to an embodiment of the present application.

FIG. 2 is a schematic perspective structural diagram of the multi-channel local shim coil unit according to an embodiment of the present application. In the present embodiment, the local shim coil 202 is fixed on the housing 201. The housing 201 may be a three-dimensional (3D) printed resin housing having a semi-cylindrical configuration and provided with a certain number of holes 203 in order to tune and match the RF receiving coil. As shown in FIG. 2, according to this embodiment, the number of local shim coils 202 is 5, the local shim coils are circular loops having a diameter of 4 cm, and the local shim coils are asymmetrically distributed. The bottom of the resin housing is further provided with a hole 205 having a diameter of 6 cm to facilitate ultrasonic ablation treatment in combination with magnetic resonance imaging techniques, and a positioning groove 204 for positioning the radio frequency receiving coil.

Figure 3:
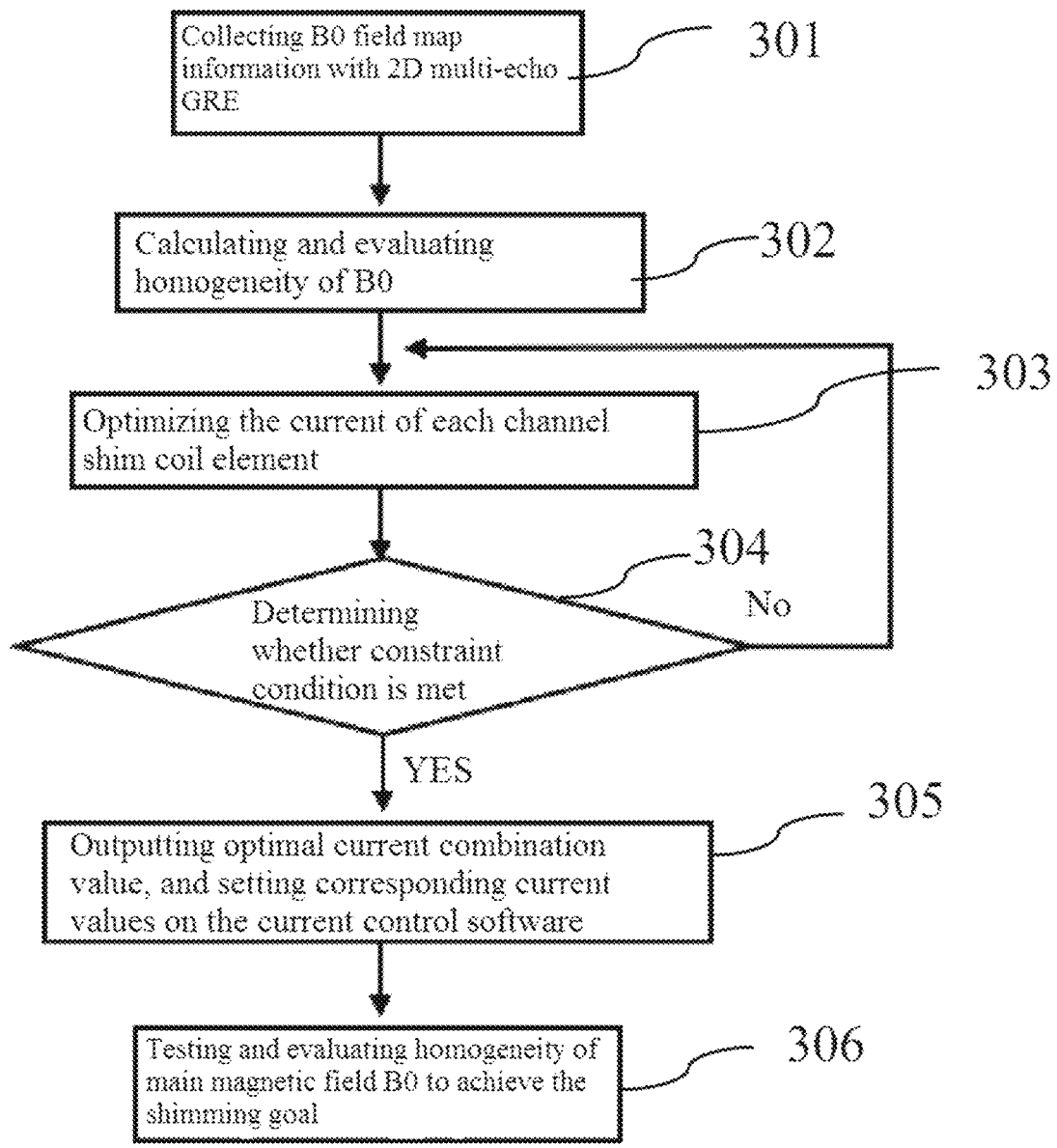
FIG. 3 is a flow chart of the shimming method for magnetic resonance imaging according to an embodiment of the present application.

FIG. 3 is a flow chart of a shimming method for magnetic resonance imaging according to an embodiment of the present application. In the present embodiment, the optimization target of the shimming is to minimize the standard deviation value of the main magnetic field offset, and the average value of the optimized main magnetic field offset is smaller than the average value of the main magnetic field offset before the optimization. In step 301, the B0 field map information is collected using a two-dimensional (2D) multi-echo GRE (gradient echo). In some embodiments, a field map is collected for each channel shimming current at 100 mA and 0 mA, and a sensitivity mapping for each channel coil is obtained after they are subtracted. In the collecting process, the number of echoes in the pulse sequence is set to 5 to reduce the effect of eddy currents on the B0 field map. In order to quickly collect field map information, the pulse sequence has a repetition time (TR) of 25 ms and the pulse flip angle is set as 10°. The homogeneity of B0 is calculated and evaluated in step 302. In some embodiments, five echo phase maps are unwrapped, and then straight-line fitting of the pixel points at the same position of the five phase maps is performed on the five corresponding echo times TE by the least square method, and the slope value is the main magnetic field offset value (in Hz) at this position. From the calculation formula $$\Delta B_0 = \frac{\Delta \phi}{\gamma \cdot \Delta TE}$$

and the formula $\Delta\omega_0 = \gamma \cdot \Delta B_0$ of the main magnetic field offset, the calculation formula of this step can be obtained as follows:

$$\Delta f = \frac{\Delta \phi}{2\pi \cdot \Delta TE},$$

wherein $\Delta\phi$ is the phase difference between the two echoes, $\gamma$ is the gyromagnetic ratio of the imaging nucleus, $\Delta TE$ is the time difference between the two echoes, and $\Delta\omega_0$ is the nuclear magnetic resonance angle frequency.

In step 303, the current of each channel shim coil element is optimized. In some embodiments, the main magnetic field offset value $\Delta f_0$ and the sensitivity field map $\Delta f_{0i}$ (i=1, 2, ..., n, wherein n is the channel number of the shim coil) of each channel shim coil element are linearly combined, which is expressed as:

$$\Delta f = \Delta f_0 + \sum_{i=1}^{n} a_i \cdot \Delta f_{0i},$$

wherein $\Delta f_0$ is the main magnetic field offset value without applying the shimming current, $\Delta f_{0i}$ is the sensitivity field map of the shim coil, $a_i$ is the linear superposition factor of the sensitivity field map, and $\Delta f$ is the main magnetic field offset value after the shimming current is applied; through the above process, with the goal of obtaining the minimum standard deviation value of $\Delta f$ to optimize the current value of each channel coil, when the average value of the optimized $\Delta f$ is smaller than the average value of $\Delta f_0$ prior to optimization, it is effective shimming.

In step 304, it is determined whether a constraint condition is met. If not, operations 303-304 are repeated until the constraint condition is met. In step 305, an optimal current combination value is output, and optimum current values corresponding to every channel shim coil are set on the current control software. Finally, in step 306, the homogeneity of the main magnetic field B0 is tested and evaluated. The average value and the standard deviation value of the main magnetic field offset value are used as the evaluation index. The smaller the value is, the more uniform the main magnetic field B0 is, and the shimming goal is achieved.

Figure 4A:
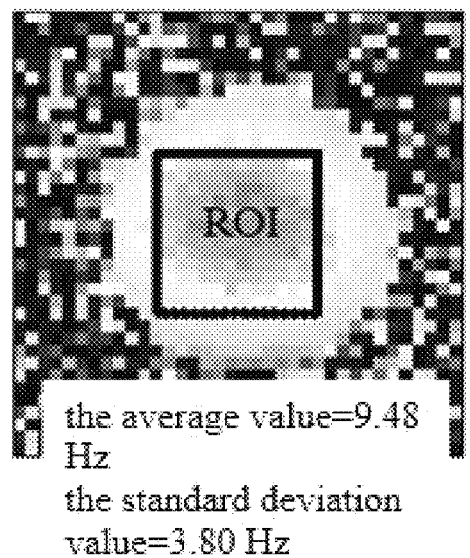
FIGS. 4A and 4B show the comparison of the obtained main magnetic field offset distributions after shimming and before shimming, respectively.
Figure 4B:
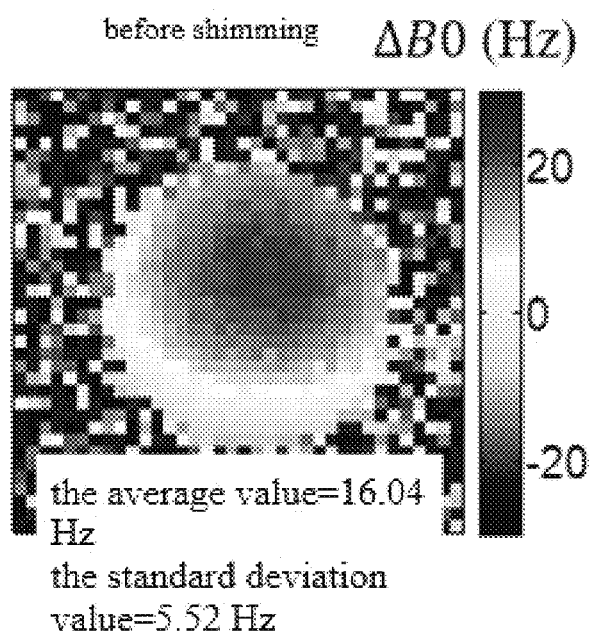
Figure 5A:
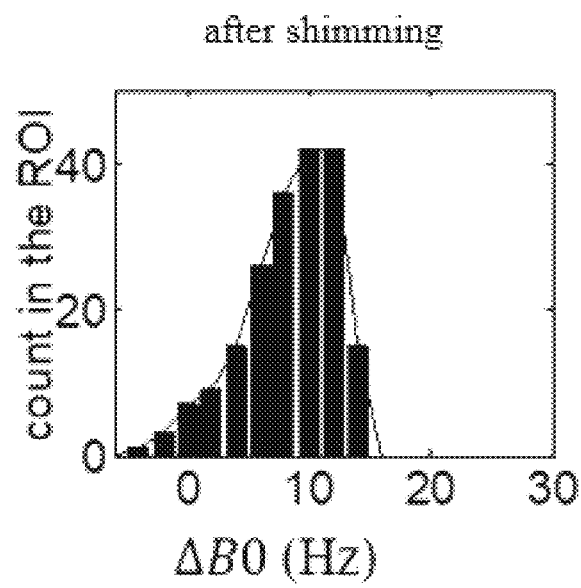
FIGS. 5A and 5B show statistics of the magnetic field frequency distributions within the region of interest ROI after shimming and before shimming, respectively.
Figure 5B:
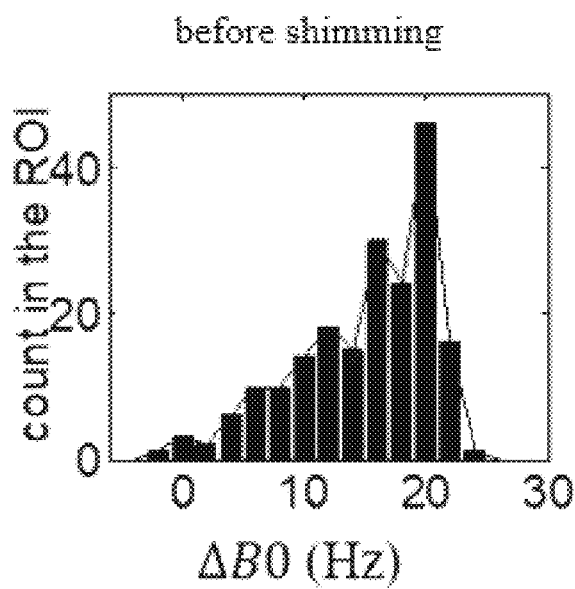
Figure 6A:
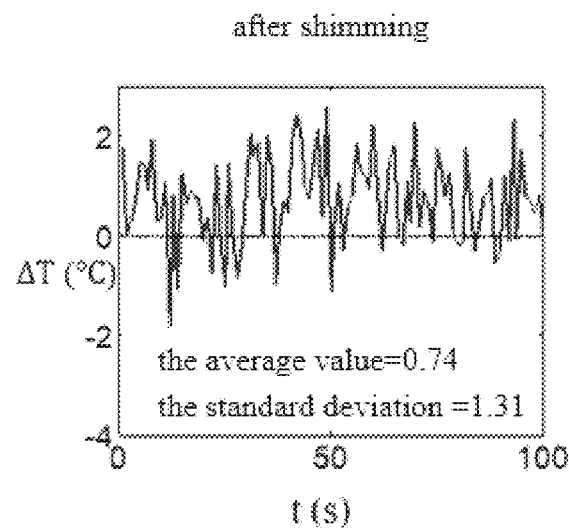
FIGS. 6A and 6B show the temperature change graph of a phantom at normal temperature conditions after shimming and before shimming, respectively.
Figure 6B:
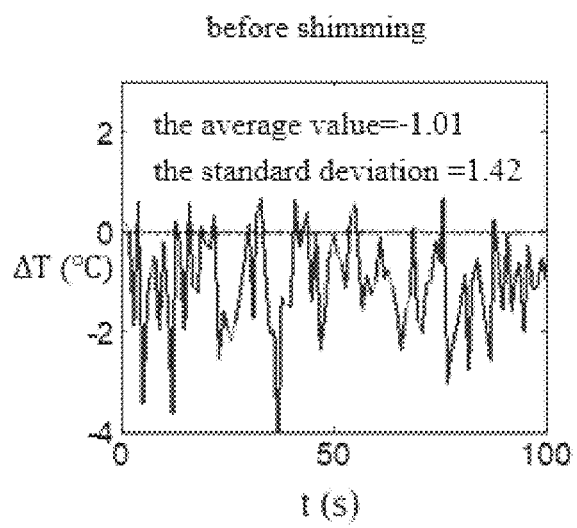

The present application is experimentally verified on a Siemens 3T magnetic resonance imaging system, and a local shimming system and a shimming method are applied in magnetic resonance temperature measurement imaging. FIGS. 4A and 4B show the comparison of the obtained main magnetic field offset distributions after shimming and before shimming (i.e., in the cases of applying the optimally combined shimming current and applying no shimming current), respectively. Before and after shimming, the average value of the main magnetic field offset values decreases from 16.04 Hz to 9.48 Hz, and the standard deviation value decreases from 5.52 Hz to 3.80 Hz. The result shows that the homogeneity of the main magnetic field is obviously improved, wherein ROI represents the region of interest. FIGS. 5A and 5B show statistics of the magnetic field frequency distributions within the region of interest ROI after shimming and before shimming, respectively, wherein the more concentrated the frequency distributions, the higher the homogeneity of the main magnetic field B0. FIGS. 6A and 6B show the temperature change graph in the phantom experiments at normal temperature conditions after shimming and before shimming, respectively. Within 100s, the average value of the temperature change before and after shimming decreases from 1.01 degrees Celsius to 0.74 degrees Celsius, and the standard deviation value decreases from 1.42 degrees Celsius to 1.32 degrees Celsius. The result shows that the temperature measurement accuracy after shimming is improved. The above experimental results show that the local shimming system and the shimming method produced by the present application can improve the homogeneity of the main magnetic field B0 and improve the accuracy of magnetic resonance temperature measurement at the same time.

The present application provides a 5-channel local shim coil for magnetic resonance temperature imaging, which compensates for a change in local magnetic field due to the difference in magnetic proton susceptibility between water and fat tissue, thereby improving the precision and accuracy of temperature measurement. The magnetic resonance shimming system and the shimming method of the embodiment of the present application achieve a better shimming effect using a shim coil with a smaller number of channels, and the system is simpler and the cost is relatively low; and the shimming method provided is relatively simple and is relatively short in time; at the same time, the system is applicable in magnetic resonance temperature imaging, which improves the accuracy of temperature measurement.

Although the present application has been described in terms of the preferred embodiments, modifications, replacements, and various alternatives are possible that fall within the scope of the present application. It should also be noted that there are many alternative ways of implementing the method and system of the present application. Accordingly, it is intended that the appended claims be interpreted as including all such modifications, replacements, and various alternatives that fall within the gist and scope of the present application.

What is claimed is:

1. A shimming system for magnetic resonance imaging, which comprises:
    a multi-channel local shim coil unit, which is configured to be installed on an inspection table of a magnetic resonance imaging system, wherein the multi-channel local shim coil unit comprises a local multi-channel shim coil and a radio frequency receiving coil for receiving magnetic resonance signals, and the radio frequency receiving coil is placed inside the local multi-channel shim coil and separated by a distance from the local multi-channel shim coil;
    a computer control system, which is configured to install and set software controlled by a DC power and calculate field maps and calculate optimization processes; and
    a DC power system, which is communicatively connected to the computer control system to control a value of current of each channel;
    wherein the multi-channel local shim coil unit further comprises a housing, the housing has a semi-cylindrical configuration, and the local multi-channel shim coil is only distributed on a semi-cylindrical surface of the semi-cylindrical configuration of the housing;
    wherein the housing has a bottom provided with a hole as a reserved channel for ultrasound ablation treatment and the bottom is also provided with a positioning groove for positioning the radio frequency receiving coil.

2. The shimming system of claim 1, wherein the housing is provided with a plurality of holes for tuning and matching the radio frequency receiving coil.

3. The shimming system of claim 1, wherein the multi-channel local shim coil unit comprises 5 channels of local shim coils, and the local shim coils are asymmetrically distributed.

4. The shimming system of claim 3, wherein the local shim coil is a circular loop having a diameter of 4 cm.

5. The shimming system of claim 1, wherein the hole has a diameter of 6 cm.

* * * * *